United States Patent [19]

Cerwen

[11] Patent Number: 5,080,936
[45] Date of Patent: Jan. 14, 1992

[54] METHOD FOR THE ASSEMBLY OF POLAR-NONPOLAR-POLAR PROTEOLIPID MEMBRANES

[76] Inventor: Erik A. Cerwen, 680 63 Likenäs, S-680 63, Sweden

[21] Appl. No.: 234,497
[22] PCT Filed: Dec. 10, 1986
[86] PCT No.: PCT/SE86/00563
  § 371 Date: Aug. 9, 1988
  § 102(e) Date: Aug. 9, 1988
[87] PCT Pub. No.: WO87/03509
  PCT Pub. Date: Jun. 18, 1987

[30] Foreign Application Priority Data
Dec. 10, 1985 [NZ] New Zealand .................. 214495

[51] Int. Cl.$^5$ ............................ B05D 3/00; B05D 3/12
[52] U.S. Cl. ..................................... 427/322; 156/336; 210/653; 264/41; 264/202; 264/255; 435/7.1; 435/174; 435/177
[58] Field of Search ............... 156/242, 336; 210/496, 210/500.27, 653; 427/332; 264/41, 202, 255; 435/7.1, 174, 177

[56] References Cited

U.S. PATENT DOCUMENTS 3,736,204  5/1973  Meriwether .................. 156/242
3,892,665  7/1975  Steigelmann et al. ............ 210/490

FOREIGN PATENT DOCUMENTS 0153133   8/1985  European Pat. Off. .
0154620   9/1985  European Pat. Off. .
1490955  11/1977  United Kingdom .
85/00060 12/1985  World Int. Prop. O. .

OTHER PUBLICATIONS

*Angew. Chem.*, 93, (1981), pp. 311-331.
*Chemical Abstracts*, vol. 78, 1973, 144529n.
*Upsala J. Med. Sci.*, 82:167-181, 1977.
*Upsala J. Med. Sci.*, 81:193-200, 1976.
*Angew. Chem.*, 83, Jahrg. 1971/Nr. 17/18, pp. 672-690.
*C&EN*, Jan. 2, 1984, pp. 25-38, Janos H. Fendler, "Membrane Mimetic Chemistry".
*Chemical Abstracts*, vol. 78, 1973, 144531q.

*Primary Examiner*—Michael Lusignan

[57] ABSTRACT

A method for the formation of a proteolipid membrane based on interphase peptides according to which an interphase peptide which has formed at the boundary of an aqueous phase and a nonpolar phase of organic solvent is brought into contact with an assembly of amphiphilic compounds such that the nonpolar surfaces of the interphase peptide and of the assembly of amphiphilic compounds face each other. In addition to peptide, the membrane also contains lipid.

7 Claims, 5 Drawing Sheets

METHOD FOR THE ASSEMBLY OF POLAR-NONPOLAR-POLAR PROTEOLIPID MEMBRANES

FIELD OF THE INVENTION

This invention relates to the formation of a membrane from peptide and lipid constituents, intended for use as a structural basis for further incorporation of biomolecules carrying out a function.

The problem how to make a non-fragile polar-nonpolar-polar membrane is one of the most important ones in contemporary biochemistry. The applications of such membranes, once stable ones can be made, are numerous, and could be expected to speed up the development in fields of applied biochemistry in which the biological functions of molecular components are used artificially to generate transmembraneous electrical potentials, current, and/or fluxes of low molecular weight compounds. One such example of a potentially useful trans-membraneous gradient is the photo-mechanical energy conversion mediated by bacteriorhodopsin, in which case light is directly transformed into mechanical work (1). Another category of examples would be in vitro correspondences to cases when the plasma membrane receptors upon binding the appropriate ligands bring about, directly or indirectly, a change of the trans-membraneous potentials. The latter category of examples would include glucose receptors, glucose and amino acid transporters, membrane-bound immunoglobulins which are part of a trans-membrane potential-modulating system, receptors for growth factors, various ion channels, and other carrier molecules. Obviously, these examples are of considerable clinical and medical importance. Furthermore, other applications of bioelectricity, biopotentials and/or biocurrents, where biomolecules are used and where they have to be anchored, linked or bound to a polar-nonpolar-polar (PNP) membrane might be possible to conceive in the future.

From the above-mentioned examples of biomolecules the function of which is linked to a PNP-membrane, it is obvious that the formation of such membranes is an extremely important topic in biochemistry. Furthermore, it is obvious that any industrial applications of these biomolecules, for example photomechanica, photoosmotic or photoelectric energy conversion using bacteriorhodopsin, glucose receptor units for automatic control of glucose levels in diabetic patients, or diagnostic equipment based on immunoreceptors linked to a PNP-membrane, would depend on the type of PNP-membrane used. For these reasons, any improvement, in any respect, of the formation of PNP-membranes has considerable industrial impact, as far as the further development of applications of PNP-membranes is concerned.

DESCRIPTION OF THE PRIOR ART

The fragility of lipid bilayers is well known to researchers in the field and is primarily due to the fact that they mostly are stabilized in the plane parallel to the surface of the membrane by weak, or at least transient hydrophobic interactions, and by transient hydrogen bonds between the polar residues of the lipid. These conditions permit long range diffusion of the individual lipid molecules above the phase transition point, when the lipid is "liquid" or "fluid". Many attempts have been made and published previously to "cross-link" the lipid at its polar residues, binding it to polar, high molecular weight compounds or surfaces. These attempts present the disadvantage that the short range interactions between the individual lipid molecules will have to adapt to any long range changes of the high molecular weight cross-linker or the surface. This means, for example, that if the cross-linker or the surface expands or contracts on the long range scale, the covalently bound lipid will be forced to move in between its short range neighbours in the plane of the membrane and the lipid or any other molecules inserted into the membrane will be berturbed. This follows naturally from that the physico-chemical properties of the surface or the cross-linker and, in particular, their expansion coefficients given in per cent change of length or area per unit change of any exterior conditions such as temperature, pH, ionic strength or composition of the buffer, may not be the same as those of the lipid bilayers. Another disadvantages of using a long-range cross-linker or surface external to the lipid bilayer is that any transmembraneous events, such as fluxes and/or changes of electrical potential, will not easily be recorded, due to the presence of the extra diffusion barrier.

It is well known that many natural membranes are lipid bilayers and that the biological function of many molecular components can be recovered by inserting them into lipid bilayers. In some cases, this requires that certain lipid species are present or that the lipid is "fluid". There are many known methods of forming lipid bilayers which can be subject to experimentation, such as the sonication of phospholipid, producing lipid vesicles, the formation of planar "black membranes" and the "patch clamp" technique for making a small area of bilayer membrane. As was mentioned above, the disadvantage of these techniques is the fragility of lipid bilayers, which becomes manifest as soon as a large area of membrane is to be assembled. Another disadvantage of pure lipid bilayers when considered for medical use in the body is the tendency of such lipid to bind to other components present there. It is well known, for example, that lipid binds to albumin and the various lipoproteins present in plasma. Of course, this leads to that the lipid disappears from any structure where it would have been placed to form a membrane as soon as that structure is placed inside the body.

From what has been mentioned above, it is obvious that it is desirable to search for an alternative to the lipid bilayer as a thin compartmentalizing PNP-membrane.

In contrast to the case of pure lipid bilayers, it has been suggested that biomembranes would exist which are stabilized by long-range covalent bonds and/or hydrogen bonds provided by amphiphilic "interphase peptides" which are shared by the hydrophilic and the hydrophobic phases of the boundary (2, 3). The finding that certain peptides, notably poly-L-lysine, adheres to solid hydrophobic surfaces (4) provides experimental support that interphase peptides partitioning at the boundary between the hydrophilic and hydrophobic phases exist, whatever their secondary or tertiary configuration may be. (Poly-L-lysine is a highly hydrophilic substance, yet it binds to hydrophobic surfaces). In the original theory of "interphase peptides" (2, 3) it has been suggested that they are stabilized by hydrophobic contact with other peptides and/or lipid, which is in accordance with the so called "hydrophobic effect", and would thus seem to be thermodynamically possible. ("The hydrophobic effect" is a term denoting the finding that polar and nonpolar solvents form separate phases). In addition, it has been suggested (2, 3) that interphase peptides are stabilized by hydrogen bonds and salt bridges. These features will allow the membrane to have many properties similar to those of lipid bilayers (3).

That interphase peptides are thermodynamically stable or, more precisely, in accordance with the hydrophobic effect means that according to the original theory, conditions would be possible to establish when they form spontaneously at a hydrophobic—hydrophilic interphase. Since hydrophobic interactions are predominantly van der Vaals interactions involving fluctuating dipole moments of almost equivalent nonpolar groups of adjacent micelles, the formation of an interphase peptide at a hydrophobic surface of a solid or at that of a liquid would not be expected to be qualitatively different from each other. However, due to the thermal agitation within a nonpolar liquid, it can be anticipated that the formation of an interphase peptide at such a boundary would take longer time than at the boundary of a nonpolar solid.

From what has been said so far, briefly describing the state of the art in the field of PNP-membranes and their industrial potential, it is obvious that present techniques need to be improved if the possible applications of such membranes are to be realized.

SUMMARY OF THE INVENTION

The present invention describes a method to assemble a core structure of a membrane based on interactions between interphase peptides and lipid, without any claim regarding the detailed applications of such a membrane. The method described will be possible to optimize. As for future applications of the method, many techniques have been published on how to incorporate functional proteins into lipid monolayers or lipid bilaters, and on the conditions which are suitable for this. Since the membrane described here is partly based on lipid, it can be anticipated that future attempts to incorporate functional proteins into it would rely, at least partly, on previous work on lipid monolayers or bilayers. While the lipid bilayer is appreciated for its tight sealing perpendicular to the plane of the membrane the proteolipid membrane described here provides stability parallel to the plane of the membrane without any claim regarding the intactness of the membrane. This is accomplished by a method for the assembly of a polar-nonpolar-polar proteolipid membrane according to which an interphase peptide which has been formed at the boundary between an aqueous phase and a nonpolar phase of organic solvent is brought into physical contact with an assembly of amphiphilic molecules forming a surface, in such a way that the nonpolar surfaces of the interphase peptide and of the assembly of amphiphilic molecules face each other. In addition to peptide, the membrane also contains lipid.

DESCRIPTION OF THE PREFERRED EMBODIMENTS

Figure 1:
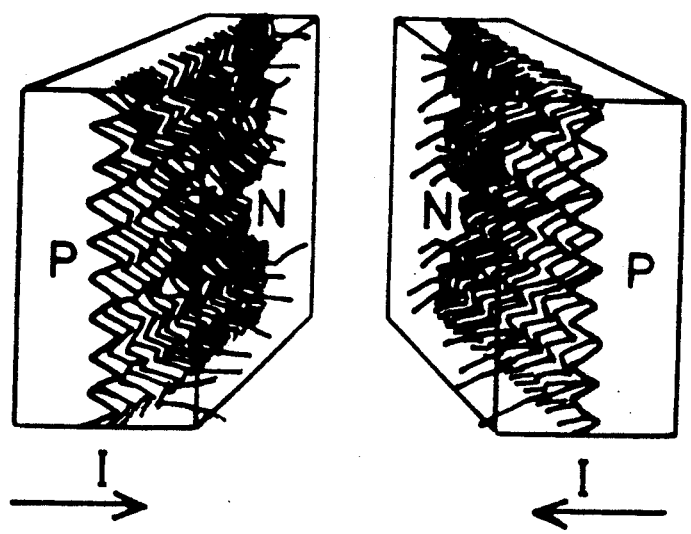
FIG. 1. Illustration of an interphase peptide providing long range structure in the form of covalent bonds extending parallel to the plane of the membrane which has been formed at the boundary of an aqueous phase and a nonpolar phase of organic solvent and which forms a layer, an interphase membrane, or part of a proteolipid membrane (left hand side block diagram) which is being brought into physical contact (arrows) with an assembly of amphiphilic molecules forming a surface (right hand side block diagram) and wherein the nonpolar surfaces of the interphase peptide and of the assembly of amphiphilic molecules face each other. The intersection of the surfaces and their extension into the plane of the block diagram is shown and the illustration is not intended to be to scale or to depict any factual arrangement at the molecular level at higher resolution than with respect to the location of the bulk phases. N=nonpolar phase. P=polar phase. I=interphase peptide.
Figure 2:
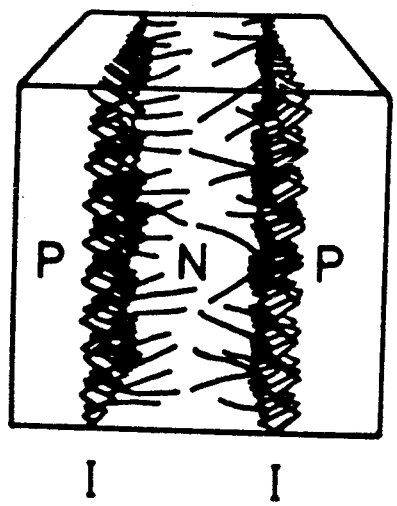
FIG. 2. Illustration of a polar-nonpolar-polar proteolipid membrane which has been assembled as a result of the hydrophobic effect from the interphase membrane and the assembly of amphiphilic molecules illustrated in FIG. 1. The intersection of the surfaces and their extension into the plane of the block diagram is shown and the illustration is not intended to be to scale or to depict any factual arrangement at the molecular level. N=nonpolar phase. P=polar phase. I=interphase peptide.

The interphase peptide is formed from a solution of poly-L-lysine (4-5 g/l), MW 15-30, or specifically 20-24 in 0.4M KOH at approximately 0° C. on top of which ethyl ether is layered. The aqueous phase conditions are essentially those given in previously published experiments (4), the only different being that the solid hydrophobic surface has been replaced by a liquid one. Since interphase peptides are thermodynamically stable (3), these conditions would not be critical, and other conditions suitable for the formation of interphase peptides would be possible to establish by any skilled experimentalist who has knowledge of the chemical and physical properties of the peptide at various pH values and for all ranges of molecular weights. The incubation at approximately 0° C. is continued until a layer of interphase peptide is detectable, for example by visual inspection. This may require that the incubation at 0° C. is continued for approximately a week, using the specified conditions. It is advisable to interrupt the incubation before the peptide is folded into the organic phase so that the membrane becomes rough on the nonpolar side. The conditions given are probably not the best for settling a stable interphase peptide and would be possible to optimize by modulating the ionic strength, the temperature, any other variable or the choice of organic solvent.

The experiments can be carried out such that one ml of organic solvent is layered on top of one ml of aqueous phase in a cylindrical glass vial of 9 mm diameter having a flat bottom. On the bottom in the aqueous phase and below the phase boundary has been placed (before the solvent is added) a cylindrical tube the upper end onto which has been stretched and glued a porous supporting membrane and along one side of which has been attached a long glass capillary extending to the top of the glass vial to serve as a handle. The tube should not be made from teflon or any other material which strongly adsorbs polylysine. The purpose of this devise is to lift the interphase membrane from below after it has formed and it should be devised in such a way that there is no vigorous movement of liquid in the aqueous phase below the membrane when it is lifted from the surface of the remaining liquid. It is desirable that the supporting membrane is smooth and that the pores in it are small since such conditions will decrease the probability that cracks appear in the interphase membrane when it is lifted. It is possible to avoid that the liquid inside the tube drops out of the tube when it is lifted, by making the lower end of the tube more narrow than its average inner diameter.

The present invention does not relate to the type of supporting membrane used and many choices are possible. A most simple and readily available choice is the transparent membrane which is used in the household for protecting food and is known under various commercial names such as "glad-wrap", surround-wrap" or "handiwrap". This type of membrane may be chosen for the experiments and glued onto the above-mentioned tube with alkali-resistant glue after which it is perforated with a needle as sharp-pointed as possible. For further optimation, it is desirable to select membranes which are smooth and have smaller pores. If the interphase peptide is formed from an alkaline solution, the supporting membrane should be alkali-resistant. The purpose of using porous supporting membranes is that trans-membraneous events taking place across the interphase membrane will be possible to record using standard techniques.

The membrane or the devise which have been described are not optimal but merely a convenient way for any handy person to lift a planar interphase membrane from a surface or an interphase. It is desirable to make the devise smaller since this will decrease the probability of cracks in he interphase membrane, but on the other hand, this might require that the whole process of lifting the membrane is performed using some standard micro-manipulator. As described above, the tube has a diameter of 5 mm and a height of 8 mm. One advantage of the devise that has been described is that is that the nonpolar part of the interphase membrane is exposed and can be sealed to any other similarly formed membrane, the nonpolar part of which is exposed. Due to the "hydrophobic effect", the two membranes, one of which contains the interphase peptide, will bind to each other, this being the essential feature of the invention. Many other types of devises can also be imagined, which would accomplish the same thing.

In addition to poly-L-lysine, it is conceivable that other peptides having the property of forming an interphase boundary exist or will be discovered in the future. The present invention would be applicable irrespective of type or molecular weight of the interphase peptide, although in each particular case, the optimal experimental conditions would be expected to be different. A necessary condition would, of course, be that any significant amount of interphase peptide is formed and that some of it stays at the boundary (or the surface of the aqueous phase) during subsequent experimental steps.

A significant advantage of using either in the method described, as compared to many other organic solvents, is that it easily can be evaporated, leaving the hydrophobic part of the interphase open to air. Another organic solvent which is not volatile could be expected to be more difficult to remove and might thicken the nonpolar part of any PNP-membrane of which it forms a constituent to the extent that it would be impossible for inserted functional molecules to carry out any vectorial trans-membraneous function. However, it would be possible to use other organic solvents if they can be replaced with a volatile solvent after the interphase peptide has formed. This follows from the near equivalence of hydrophobic bonding, which involves fluctuating dipole moments (van der Vaals forces) irrespective of the chemical composition of the compound. Therefore, it is obvious that the basic mechanisms of the formation of a thermodynamically stable (cf. 3) interphase peptide are not altered if the choice of organic solvent is altered, as long as the solvent does not contain any amount of polar groups. Also the shape of the solvent molecules will be of importance and it is advisable to check each solvent for its suitability to bind the peptide.

According to the present invention, the interphase peptide is incubated with lipid. In this context, lipid is regarded in its widest sense, as a group of amphiphilic elongated compounds composed of at least one polar group at one end and at least one nonpolar group at the opposite end, which definition may include, for example, certain detergents.

The rationale for incubating the peptide with lipid is that the spreading of the interphase configuration in the plane of the boundary between the nonpolar and polar phase is restricted by the constraints of the possible angles of covalent bonding and it is expected that a membrane based solely on peptide would be porous. Furthermore, the binding blocks of the peptide are considerably larger than those of lipid monomers in lipid bilayers, and tight fitting between the peptide building blocks down to the atomic level can not be anticipated. In the original theory of membranes based on interphase peptides (2, 3), the membranes are stabilized not only by hydrophobic interactions but also by the more specific hydrogen bonds and salt bridges. According to the present invention, this is allowed for by incubating the peptide with lipid, which, according to the original theory, stabilizes the membrane by interacting with the peptide in the nonpolar plane, a plane of hydrogen bonding, and a plane of salt bridges (3). None of these interactions is a covalent bond, which allows a certain flexibility of movement of the compounds forming the membrane, similarly to the case of lipid bilayers.

The lipid is added in the organic phase either in a few ul of chloroform - methanol or in a few ul of ether or in any other suitable solvent. If a heterogeneous mixture of lipid is used, many different kinds of interactions between the lipid and the protein will be possible and the chances are better that the pores between the amino acid units are filled out. However, any type of amphiphilic lipid capable of settling at the polar-nonpolar boundary will fill out the pores and improve the fitting between the various residues. It should be remembered that there is competition for the boundary by the peptide and the lipid and if too much lipid is added, it may completely replace the peptide. A heterogenic mixture of lipid can, for example, be prepared by dissolving one egg yolk to a total volume of 100 ml in 10 mM potassium phosphate buffer, pH 7.4, containing 0.15M of potassium chloride, mixing it with 100 ml of chloroform - methanol (2:1), then extracting 50 ml of this mixture with 100 ml of chloroform and filtering the organic phase through several (5) layers of filter paper so that it becomes clear. The resulting clear organic phase can be used in the method described here. However, the extraction of lipid from various raw materials has been well described in the literature and many other ways to prepare lipid are known. In particular, lipid fractions containing less cholesterol than the one specified above can be obtained and used for the present invention.

The lipid is added to the organic phase after the interphase peptide has formed or while it is being formed, as long as it does not interfere with its formation. Using the conditions specified above, it is added to the organic phase after approximately 10 days of incubation with the poly-L-lysine, and the incubation at 0° C. is then continued overnight. Excess lipid is then removed by carefully replacing the organic phase several times with pure ether.

The addition of lipid to the organic phase is convenient and preferable to adding it in the aqueous phase, in which case it may form micelles and may not enter the boundary due to steric hindrance from the peptide or electrostatic factors. However, whether the lipid is added from the aqueous phase or the organic phase is not critical for the present invention as long as it does not dissolve the interphase peptide into the polar or nonpolar phases. Various types of lipid can be expected to fill out existing pores more or less efficiently and the method has yet to be optimized in his respect. To make a stable membrane, it is desirable to optimize the nonpolar interactions, the hydrogen bonding, and the salt bridges within the membrane, as stated in the original theory (3). A way of doing this is to select a heterogeneous mixture of lipid and expect that the best fitted lipid will settle at the boundary and that the final proteolipid boundary will represent the thermodynamically most stable condition, excluding un-fitted lipid species. Of course, once the interacting lipid species can be identified, they can be added specifically in well-defined amounts, but this will hardly affect the mechanisms of the formation of the proteolipid membrane, which is formed as a result of thermodynamic forces.

After formation of the proteolipid membrane, excess organic solvent is evaporated or aspirated, leaving the interphase under the meniscus, and the proteolipid membrane is lifted out of the incubation vessel. This should be done in a cold room, preferably keeping 0°-2° C. In one realization of the invention, the thus formed proteolipid membrane is joined to a similarly formed proteolipid membrane which has been collected on another supporting membrane and another lifting devise of the same type, in such a way that the nonpolar parts of the proteolipid membranes are brought into contact. It should be remembered that when the ether has evaporated, one important factor in keeping the proteolipid membrane together is lost and it is desirable to join the two membranes as soon as possible. On the other hand, if there is still a significant amount of organic solvent on the nonpolar side of any of the two proteolipid membranes, it will be included in the PNP-membrane and make it thicker. If, subsequently, the organic solvent is equilibrated out of the membrane, the latter may be perturbed.

An advantage of the method of the invention which has been described is that the formed PNP-membrane will automatically be connected to two aqueous phase chambers which can be modified for further experimentation and optimization of the invention. The two pieces of tube would be possible to prepare for various types of standard biochemical and biophysical experimentation. In particular, they can be made in such a way that they seal tightly along the circumference after the PNP-membrane has formed, using, for example, a clamp mechanism.

However, many other methods to join a peptide (-lipid) membrane to an assembly of amphiphilic compounds, which is an essential feature of the invention, can be imagined. The advantage of a PNP-membrane in which interphase peptides form an essential part, according to the method described, as compared to lipid bilayers, is that the membrane containing interphase peptides is stabilized in the plane parallel to its surface by covalent bonds which extend continuously for a longer distance than the average diameter of the lipid of lipid bilayers. This is a requirement for the poly-L-lysine to partition at the boundary of a nonpolar surface, as it is known to do (4) and is evident for the naked eye in the method described by the high viscosity of the interphase membrane based on peptide as opposed to that of an interphase based on the described lipid mixture (added in chloroform - methanol) only. In the former case, any irregularities or particles at the interphase will retain their approximate relative location even if the glass vial is gently agitated by hand. This clearly shows that there is long range structure in the plane of the membrane bordering the nonpolar phase when the peptide is there as opposed to the case when only lipid has access to the boundary between the polar and nonpolar phases. When the nonpolar phase is subsequently replaced with another membrane such that the two membranes are joined by hydrophobic bonding, this state of acts is, due to the near equivalence of hydrophobic bonding irrespective of chemical compound, not qualitatively changed. The advantage of an interphase peptide providing long-range structure in the form of covalent bonds extending parallel to the plane of the membrane is, of course, that it will stabilize the whole membrane by providing permanent covalent bonds instead of transient hydrophobic bonding or hydrogen bonding. Above the melting point of the lipid when the latter is "fluid" and "liquid" and tends to diffuse away in any lipid bilayer structure where it is a constituent, such stabilization by covalent bonds would be particularly important for maintaining a structure in the plane of the membrane.

Thus, while the lipid bilayer is appreciated for its tight sealing perpendicular to the plane of the membrane, the proteolipid membrane described here provides stability parallel to the plane of the membrane without any claim regarding the intactness of the membrane. The membrane described may contain pores and/or cracks the amount of which may vary depending on the skill of the experimentalist. Therefore, the membrane should be regarded as a PNP-membrane with a predominantly nonpolar core and suitable for optimization of its sealing perpendicular to its plane, as well as of its stability parallel to the membrane.

In addition to joining the proteolipid membrane to another similarly formed membrane, it can be joined to a lipid monolayer formed in a conventional way on the surface of an aqueous solution and pressed together to form as high a density of lipid per surface unit as possible. The aqueous phase should have approximately the same ionic strength and pH as that on the polar side of the proteolipid membrane. The joining together of a proteolipid membrane as described with a conventional lipid monolayer such that their nonpolar surfaces face each other follows the same principles (the hydrophobic effect) as does the joining together of two proteolipid membranes as described previously.

The PNP-membrane described in the method of the invention may be subject to limited proteolytic digestion after its formation. Then, the composition of the buffer should be such that it does not destabilize the membrane.

References

1. R. C. Srivastave et al.: Experientia 40 (7), 773-775 (1984)
2. E. Cervén: Upsala J. Med. Sci. 81, 193-200 (1976)
3. E. Cervén: Upsala J. Med. Sci. 82, 167-181 (1977)
4. S. S. Brown: Methods in Cell Biology. Vol 24, Pt. A (Ed: L. Wilson), pp. 291-300, Academic Press, New York, London, Paris, San Diego, San Fransisco, Sao Paulo, Sydney, Tokyo, Toronto (1982)

I claim:

1. A method for the assembly of a polar-nonpolar-polar proteolipid membrane according to which an interphase peptide which has been formed at the boundary between an aqueous phase and a nonpolar phase of organic solvent forms a layer, an interphase membrane or part of a proteolipid membrane, and said layer or membrane containing the interphase peptide is stabilized in its plane by the interphase peptide and according to which said interphase peptide stabilizing the formed layer or membrane is brought into physical contact with an assembly of amphiphilic molecules forming a surface the nonpolar surface of which faces the nonpolar surface of the interphase peptide, and the polar-nonpolar-polar membrane is formed using the hydrophobic effect join the two nonpolar surfaces.

2. A method as claimed in claim 1, wherein the interphase peptide has been incubated with lipid.

3. A method as claimed in claim 2, wherein the lipid is a mixture of lipid species.

4. A method as claimed in claim 2 or claim 3 wherein the lipid has been derived from egg yolk.

5. A method as claimed in any one preceding claim, wherein the interphase peptide has been derived from poly-L-lysine.

6. A method for the assembly of a polar-nonpolar-polar proteolipid membrane as claimed in claim 1, wherein the interphase peptide which has formed at the boundary of an aqueous phase and a nonpolar phase of organic solvent forms a layer, an interphase membrane, or part of a proteolipid membrane, and said layer or membrane containing the interphase peptide and being stabilized in its plane by the interphase peptide, after its formation is brought into physical contact with an assembly of amphiphilic molecules forming a surface using the hydrophobic effect, and using a devise or devises join the nonpolar surfaces of the interphase peptide and of the assembly of amphiphilic molecules, and the devise is composed of a tube the upper end onto which has been stretched and glued a porous supporting membrane and along one side of which has been attached a handle, and two such devises are used to collect the interphase membranes from below after their formation, and after lifting the devises, the polar-nonpolar-polar proteolipid membrane is formed by joining the devises, the nonpolar surfaces of the interphase membranes facing each other and the polar-nonpolar-polar proteolipid membrane is formed as a result of the hydrophobic effect.

7. A method as claimed in claim 5 wherein the interphase membrane is formed by incubating poly-L-lysine in alkaline solution on top of which has been layered ethyl ether and the incubation is carried out for approximately a week at 0° C.

* * * * *

UNITED STATES PATENT AND TRADEMARK OFFICE
CERTIFICATE OF CORRECTION

PATENT NO. : 5,080,936  
DATED : January 14, 1992  
INVENTOR(S) : Erik Cerwen

Page 1 of 1

It is certified that error appears in the above-identified patent and that said Letters Patent is hereby corrected as shown below:

Column 1,  
Line 46, "photomechanica" should read -- photomechanical --.

Column 2,  
Line 12, "berturbed" should read -- perturbed --.  
Line 19, "disadvantages" should read -- disadvantage --.

Figure 3:
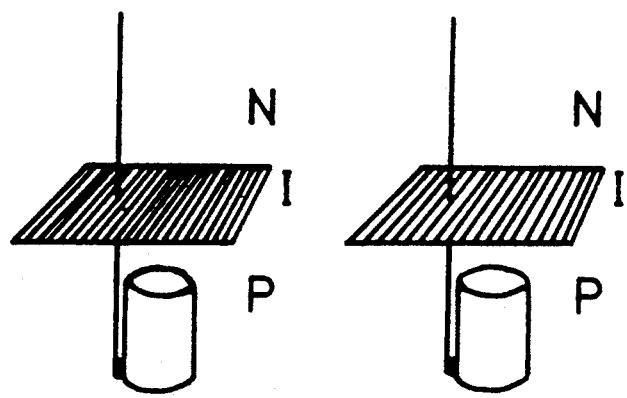
FIG. 3. ((Brief Description of Drawing 2.)) Illustration of the lifting devise when it is kept in the aqueous phase until the interphase membrane has formed.
Figure 4:
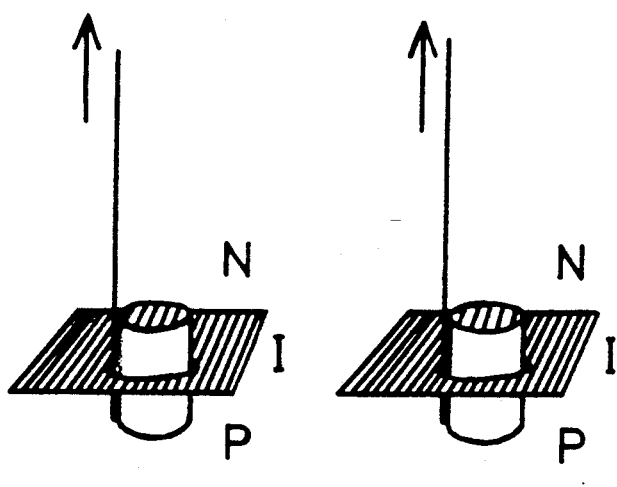
FIG. 4. Illustration of the lifting devise when it is lifted through the interphase membrane mentioned in FIG. 1 and FIG. 3 to collect the interphase membranes from below after their formation.
Figure 5:
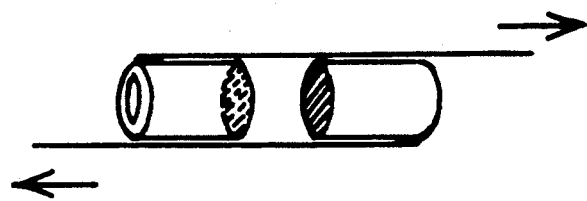
FIG. 5. Illustration of the lifting devise when it is used to join the interphase peptide mentioned in FIG. 1 and FIG. 3 to an assembly of amphiphilic molecules forming a surface such that the nonpolar surfaces face each other.

Column 4,  
Line 21, "FIG. 3 ((Brief Description of Drawing 2))" should read -- FIG. 3 --.  
Line 37, "MW 15-30" should read -- MW 15.000 - 30.000 --.  
Line 38, "20-24" should read -- 20.000 - 24.000 --.  
Line 41, "different" should read -- difference --.

Column 5,  
Line 41, "he" should read -- the --.  
Line 66, "either" should read -- ether --.

Column 7,  
Line 28, "his" should read -- this --.

Column 8,  
Line 33, "acts" should read -- facts --.

Column 9,  
Line 11, "...stave" should read -- ...stava --.  
Line 35, "effect join" should read -- effect joining --.

Column 10,  
Line 19, "devises join" should read -- devises joining --.

Signed and Sealed this

Twenty-second Day of January, 2002

*Attest:*

*Attesting Officer*

JAMES E. ROGAN  
*Director of the United States Patent and Trademark Office*